(12) United States Patent
Hong

(10) Patent No.: US 12,339,525 B2
(45) Date of Patent: Jun. 24, 2025

(54) OPHTHALMIC LENS WITH PHASE-SHIFT STRUCTURE AND METHOD

(71) Applicant: Alcon Inc., Fribourg (CH)

(72) Inventor: Xin Hong, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 605 days.

(21) Appl. No.: 17/496,093

(22) Filed: Oct. 7, 2021

(65) Prior Publication Data

US 2022/0113557 A1 Apr. 14, 2022

Related U.S. Application Data

(60) Provisional application No. 63/089,146, filed on Oct. 8, 2020.

(51) Int. Cl.
*G02C 7/02* (2006.01)
*G02C 7/04* (2006.01)
*G02C 7/06* (2006.01)

(52) U.S. Cl.
CPC .............. *G02C 7/024* (2013.01); *G02C 7/022* (2013.01); *G02C 7/04* (2013.01); *G02C 7/06* (2013.01)

(58) Field of Classification Search
CPC .......... G02C 7/024; G02C 7/022; G02C 7/04; G02C 7/06; G02C 7/044; G02C 7/02; A61F 2/1618; A61F 2/1654
See application file for complete search history.

(56) References Cited

U.S. PATENT DOCUMENTS

| | | | |
|---|---|---|---|
| 8,241,354 B2 | 8/2012 | Hong et al. | |
| 9,968,440 B2 | 5/2018 | Hong et al. | |
| 10,842,617 B2 | 11/2020 | Hong et al. | |
| 2005/0128432 A1* | 6/2005 | Altmann | G02C 7/042 351/159.41 |
| 2006/0098162 A1* | 5/2006 | Bandhauer | G02C 7/042 351/159.44 |
| 2009/0234448 A1* | 9/2009 | Weeber | G02C 7/042 623/6.3 |

(Continued)

FOREIGN PATENT DOCUMENTS

| | | |
|---|---|---|
| WO | 2005098518 A1 | 10/2005 |
| WO | 2014033543 A2 | 3/2014 |
| WO | 2018100452 A1 | 6/2018 |

*Primary Examiner* — Balram T Parbadia
*Assistant Examiner* — Gabriel A Sanz
(74) *Attorney, Agent, or Firm* — Patterson + Sheridan, LLP

(57) ABSTRACT

An ophthalmic lens includes an optic with a first surface, a second surface, and a phase-shift structure having one or more phase-shift regions. A method for fabricating an ophthalmic lens includes designing an optic with a first surface, a second surface, and a phase-shift structure having one or more phase-shift regions. The phase-shift regions may be adapted to generate respective chromatic focal shifts such that an incident radiation in a respective wavelength range at least partially converges towards a respective selected wavelength. The method includes determining a chromatic aberration target for the optic and determining the quantity of the phase-shift regions meeting the chromatic aberration target. The optic is formed with the phase-shift regions having respective optimal heights obtained based in part on an overall interaction effect. The phase-shift structure may be adapted to increase a depth-of-focus of the optic in the direction of extension.

17 Claims, 6 Drawing Sheets

(56) References Cited

U.S. PATENT DOCUMENTS

| | | | |
|---|---|---|---|
| 2010/0016965 A1* | 1/2010 | Hong | A61F 2/1648 623/6.37 |
| 2010/0312337 A1* | 12/2010 | Zhang | A61F 2/1654 623/6.31 |
| 2011/0317124 A1* | 12/2011 | Weeber | A61F 2/1645 351/159.11 |
| 2013/0033676 A1* | 2/2013 | Zalevsky | G02C 7/04 351/159.01 |
| 2017/0245987 A1* | 8/2017 | Canovas Vidal | A61F 2/1618 |
| 2018/0243082 A1 | 8/2018 | Zheleznyak et al. | |
| 2019/0171036 A1* | 6/2019 | Weeber | G02C 7/044 |

\* cited by examiner

OPHTHALMIC LENS WITH PHASE-SHIFT STRUCTURE AND METHOD

CROSS-REFERENCE TO RELATED APPLICATIONS

This application claims priority to and benefit of U.S. Provisional Patent Application No. 63/089,146, filed Oct. 8, 2020, the entire contents of which are incorporated by reference herein in its entirety.

TECHNICAL FIELD

The disclosure relates to an ophthalmic lens having a phase-shift structure and a method of making the ophthalmic lens.

BACKGROUND

Humans have five basic senses: sight, hearing, smell, taste, and touch. Sight gives us the ability to visualize the world around us and connects us to our surroundings. Many people worldwide have issues with quality of vision and require the use of ophthalmic lenses. An ophthalmic lens may be worn in front of the eye, for example, in the form of contact lenses and spectacles. The ophthalmic lens may be implanted into the eye, for example, in a cataract procedure to replace a human lens that has become cloudy. The optical performance of ophthalmic lenses may be adversely affected by certain types of aberrations.

SUMMARY

Disclosed herein is a method for fabricating an ophthalmic lens. The method includes designing a phase-shift structure with one or more phase-shift regions for a first surface of an optic, the first surface being at least one of an anterior surface and a posterior surface. The one or more phase-shift regions are adapted to generate respective chromatic focal shifts such that an incident radiation in a respective wavelength range at least partially converges towards a focal position of a respective selected wavelength.

The method includes determining a chromatic aberration target for the optic and selecting a quantity of the one or more phase-shift regions meeting the chromatic aberration target, based in part on respective initial step heights of the one or more phase-shift regions. The method further includes determining an overall interaction effect of the respective initial step heights and determining respective optimal heights of the one or more phase-shift regions based in part on the overall interaction effect. The optic is formed with the one or more phase-shift regions having the respective optimal heights.

The respective initial step heights may be bounded within a minimum parameter and a maximum parameter, prior to determining the overall interaction effect. The minimum parameter may be negative 10 micron. The maximum parameter may be positive 10 micron. The optic may be formed from a cross-linked copolymer of 2-phenylethyl acrylate and 2-phenylethyl methacrylate. The normal human eye has a chromatic aberration of about 1.5 Diopters within the visible light in the wavelength range of about 450 nm and about 650 nm. The chromatic aberration target may be set within a range extending from −0.5 to 1.5 Diopters, corresponding to a chromatic aberration correction of 0 to −2.0 Diopters. The chromatic aberration target is the resultant value and the chromatic aberration correction is the compensation added to obtain the resultant value. The respective selected wavelength may include a first selected wavelength around 550 nm. The respective selected wavelength may include a second selected wavelength at or above 650 nm, and a third selected wavelength at or below 450 nm.

Forming the optic with the phase-shift structure may include forming an inner refractive region defining a first nominal optical power and an outer refractive region defining a second nominal optical power. The inner refractive region extends from an inner boundary and the outer refractive region extending from an outer boundary. The phase-shift structure is positioned between the inner refractive region and the outer refractive region, the phase-shift structure extending from the inner boundary to the outer boundary. The method may include aligning the one or more phase-shift regions in a direction of extension, the phase-shift structure being adapted to increase a depth-of-focus of the optic in the direction of extension.

Disclosed herein is an ophthalmic lens with an optic having a first surface and a second surface disposed about an optical axis. At least one of the first surface and the second surface includes an inner refractive region defining a first nominal optical power and an outer refractive region defining a second nominal optical power. The inner refractive region extending from an inner boundary and the outer refractive region extending from an outer boundary. A phase-shift structure is positioned between the inner refractive region and the outer refractive region, the phase-shift structure extending from the inner boundary to the outer boundary. The phase-shift structure includes one or more phase-shift regions defining respective optimal heights. The one or more phase-shift regions are adapted to generate respective chromatic focal shifts such that an incident radiation in a respective wavelength range at least partially converges towards a respective selected wavelength. The phase-shift structure is adapted to meet a chromatic aberration target for the optic.

The respective optimal heights may be based in part on respective initial step heights of the one or more phase-shift regions and an overall interaction effect of the respective initial step heights. The optic may be an intraocular lens. The optic may be a contact lens. The respective chromatic focal shifts may extend between about −0.5 and 1.5 Diopters for incident radiation extending in a wavelength range of about 450 nm to about 650 nm.

Disclosed herein is an ophthalmic lens with an optic having a first surface and a second surface disposed about an optical axis. At least one of the first surface and the second surface includes an inner refractive region defining a first nominal optical power and an outer refractive region defining a second nominal optical power. The inner refractive region extending from an inner boundary and the outer refractive region extending from an outer boundary. A phase-shift structure is positioned between the inner refractive region and the outer refractive region, the phase-shift structure extending from the inner boundary to the outer boundary. The phase-shift structure includes one or more phase-shift regions defining respective optimal heights. The one or more phase-shift regions are aligned in a direction of extension. The phase-shift structure is adapted to increase a depth-of-focus of the optic in the direction of extension. The depth-of-focus of the optic in the direction of extension may be selected to be within a range from about 0.75 Diopter to about 3.0 Diopter.

The above features and advantages and other features and advantages of the present disclosure are readily apparent from the following detailed description of the best modes for carrying out the disclosure when taken in connection with the accompanying drawings.

DETAILED DESCRIPTION

Figure 1:
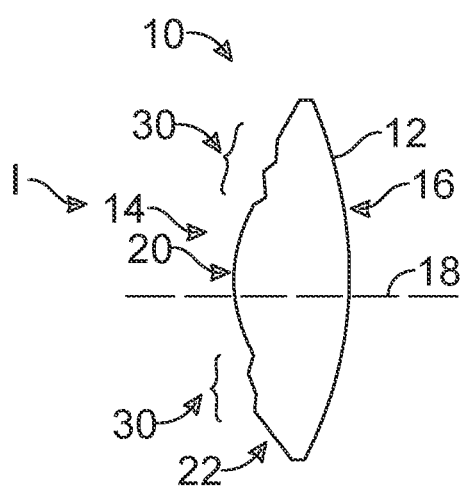
FIG. 1 is a schematic cross-sectional view of an ophthalmic lens having a phase-shift structure with one or more phase-shift regions.

Referring to the drawings, wherein like reference numbers refer to like components, FIG. 1 schematically illustrates an ophthalmic lens 10 composed of an optic 12 having a first surface 14 and a second surface 16 disposed about an optical axis 18. The first surface 14 may be the anterior surface or the posterior surface. Conversely, the second surface 16 may be the posterior surface or the anterior surface. The ophthalmic lens 10 may be an intraocular lens, a contact lens, a spectacle lens or other type of corrective lens.

Figure 2:
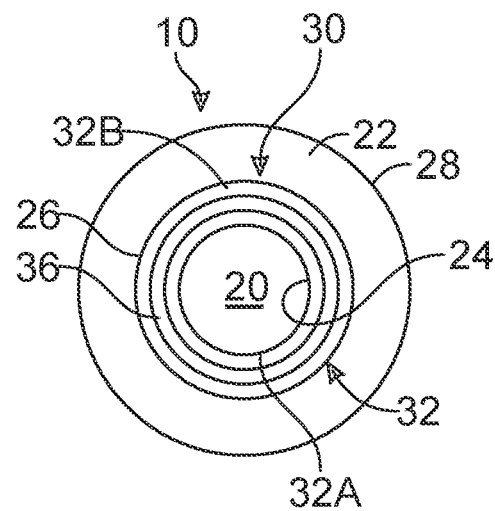
FIG. 2 is a schematic top view of the ophthalmic lens shown in FIG. 1.

FIG. 2 is a schematic top view of the ophthalmic lens 10. Referring to FIGS. 1-2, the ophthalmic lens 10 includes an inner refractive region 20 defining a first nominal optical power and an outer refractive region 22 defining a second nominal optical power. In one example, the first nominal optical power and the second nominal optical power are the same. In another example, the first nominal optical power and the second nominal optical power are different. Referring to FIG. 2, the inner refractive region 20 extends from a center of the optic 12 to an inner boundary 24, while the outer refractive region 22 extends from an outer boundary 26 to an exterior surface 28 of the optic 12.

Referring to FIGS. 1-2, phase-shift structure 30 is positioned between the inner refractive region 20 and the outer refractive region 22, the phase-shift structure 30 extending from the inner boundary 24 to the outer boundary 26. Referring to FIG. 2, the phase-shift structure 30 includes one or more phase-shift regions 32 ("one or more" omitted hereafter) each of which may define a respective initial step height. The phase-shift regions 32 may be separated by one or more plateau regions 36.

The refractive power of the lens in a human eye varies as a function of the wavelength of incident radiation. The human eye has approximately −1.2 Diopter defocus for blue wavelength (0.45 microns) and approximately 0.3 Diopter defocus for red wavelength (0.65 microns). The blue, green and red components of light are separated along the visual axis due to longitudinal chromatic aberration in the human eye. The chromatic aberration may extend approximately 1.5 Diopters over a wavelength range of 450 nm to 650 nm. This degrades the image quality observed by the human eye. As described below, the ophthalmic lens 10 utilizes the phase-shift structure 30 to reduce the chromatic aberration and improve vision quality. More specifically, the ophthalmic lens 10 is optimized to meet a chromatic aberration target. Additionally, the ophthalmic lens 10 may leverage the use of the phase-shift structure 30 to increase depth of focus.

Referring to FIG. 2, in the example shown, the phase-shift regions 32 include a first phase-shift region 32A and a second phase-shift region 32B. However, it is to be understood that the number of phase-shift regions 32 may be varied according to the application at hand. The change in the speed of propagation of the incident radiation I through the optic 12 introduces a phase-shift to the wave field. This phase-shift is proportional to the length of the path traversed by the incident radiation I. Referring to FIG. 2, the first phase-shift region 32A (see FIG. 1) may be adapted to generate respective chromatic focal shifts such that the incident radiation I in a first wavelength range at least partially converges towards a focal position of a first selected wavelength. The second phase-shift region 32B may be adapted to generate respective chromatic focal shifts such that the incident radiation I in a second wavelength range at least partially converges towards a focal position of a second selected wavelength. In one example, the respective chromatic focal shifts extend between about −0.5 and 1.5 Diopters for incident radiation I extending in a wavelength range of about 450 nm to about 650 nm.

Figure 3:
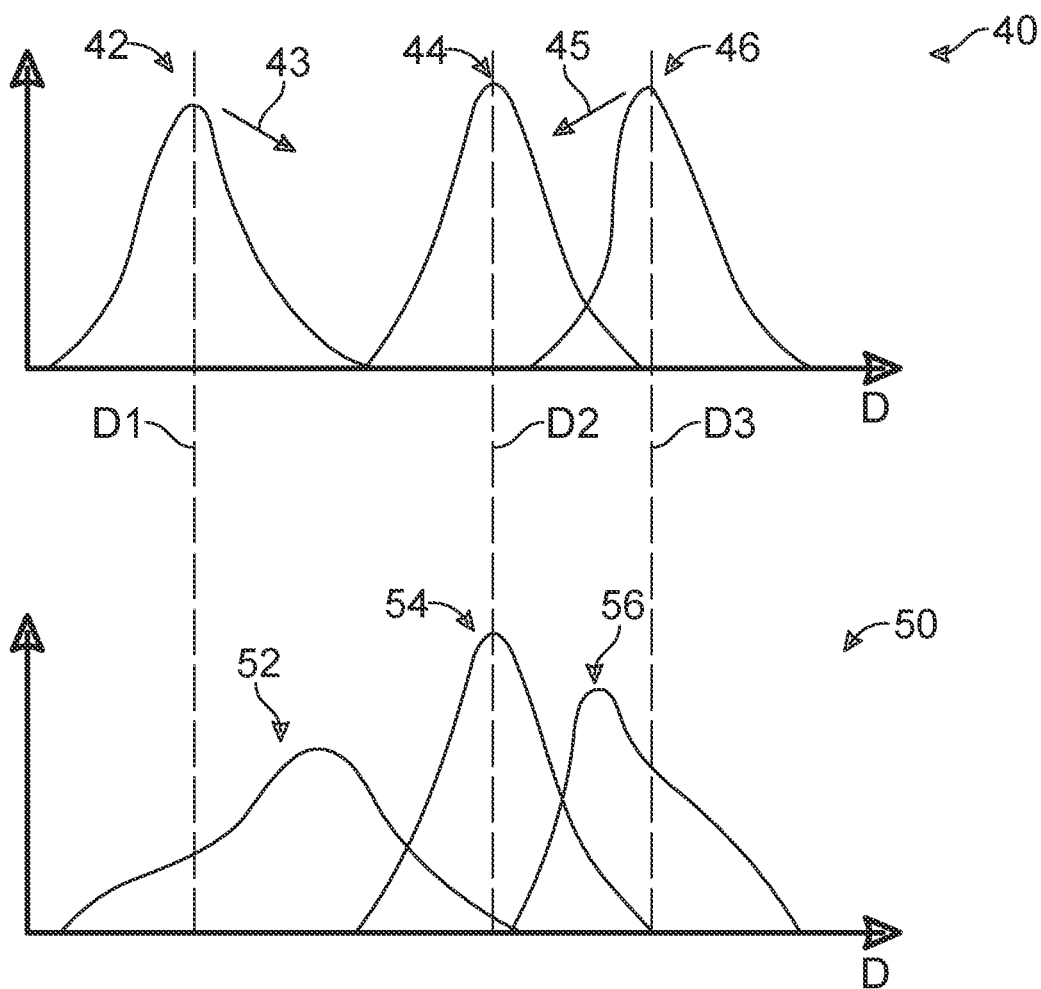
FIG. 3 is a schematic illustration of the effect of a single phase-shift region on a Modulation Transfer Function plot for an example lens.

FIG. 3 is a schematic illustration of the effect of a single phase-shift region on a Modulation Transfer Function plot for a hypothetical lens. Graph 40 of FIG. 3 illustrates Modulation Transfer Function peaks (vertical axis) in the absence of a phase-shift structure 30. The modulation transfer function is formally defined as the magnitude (absolute value) of the complex optical transfer function, which specifies how different spatial frequencies are handled by an optical system. The horizontal axis in FIG. 3 shows distance D along the optical axis 18. Graph 40 shows a first curve 42, a second curve 44 and a third curve 46, representing a first wavelength, a second wavelength and a third wavelength, respectively. In one example, the first wavelength, the second wavelength and the third wavelength are 450 nm, 550 nm and 650 nm, respectively.

The respective peaks of the first curve 42, the second curve 44 and the third curve 46 are separated along the optical axis 18 due to the effect of chromatic aberration, which reduces the quality of vision. As shown in graph 40, the respective maxima or respective peaks of the first curve 42, the second curve 44 and the third curve 46 are located at distances D1, D2 and D3, respectively, along the optical axis 18. The phase-shift region 32 causes the first curve 42 to shift in direction 43 towards the second curve 44, and the third curve 46 to shift in direction 45 towards the second curve 44, effectively reducing the chromatic aberration of the eye when the ophthalmic lens 10 is placed in front of or implanted into a human eye. Graph 50 of FIG. 3 shows the final effect of the phase-shift, with first curve 52, second curve 54 and third curve 56. As shown in graph 50, the respective peaks of the first curve 52 and the third curve 56 are shifted away from distances D1 and D3, respectively.

Figure 4A:
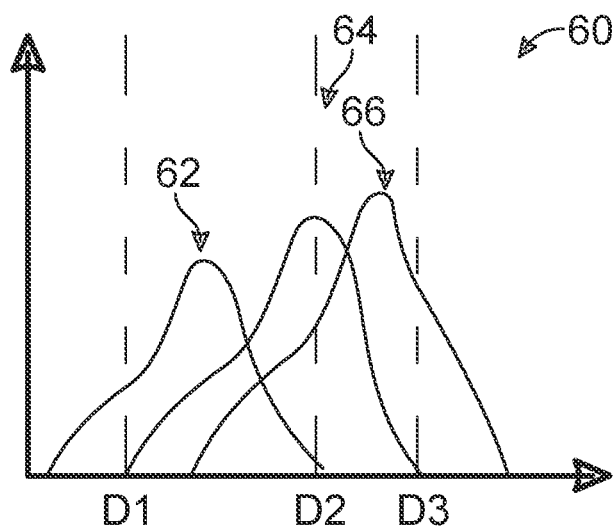
FIG. 4A is a schematic graph showing a Modulation Transfer Function plot for a phase-shift structure incorporating two phase-shift steps.

FIG. 4A is a schematic graph showing a Modulation Transfer Function plot for a phase-shift structure with two phase-shift regions. In some embodiments, the incorporation of a phase-shift structure with two phase-shift regions, as opposed to a single phase-shift region, may allow for a greater convergence of peaks corresponding to incoming radiation of different wavelengths. Portion 60 of FIG. 4A shows an example Modulation Transfer Function plot for an ophthalmic lens 10 with a two-step phase-shift structure 30. Without phase-shifting, the respective peaks of the first curve 62, second curve 64 and third curve 66 are at distances D1, D2 and D3 along the optical axis 18, respectively. As shown in portion 60, the depth of focus is extended with a two-step phase-shift design; the peak of the first curve 62 is moved towards the peak of the second curve 64, extending the depth of focus. With the same optimal steps, the peak of the third curve 66 is moved towards the peak of the second curve 64. Stated differently, the focal positions defined by the wavelengths in the range between the wavelengths of the first curve 62 and the wavelength of the third curve 66 are at least partially converged towards a focal position defined by the wavelength of the second curve 64, referred to herein as the first selected wavelength. The first selected wavelength may be at or below a first threshold. For example, the first threshold may be 550 nm. Alternatively or additionally, the focal positions defined by the wavelengths of the first curve 62 and the third curve 66 may be at least partially converged towards one or more other focal positions.

Figure 4B:
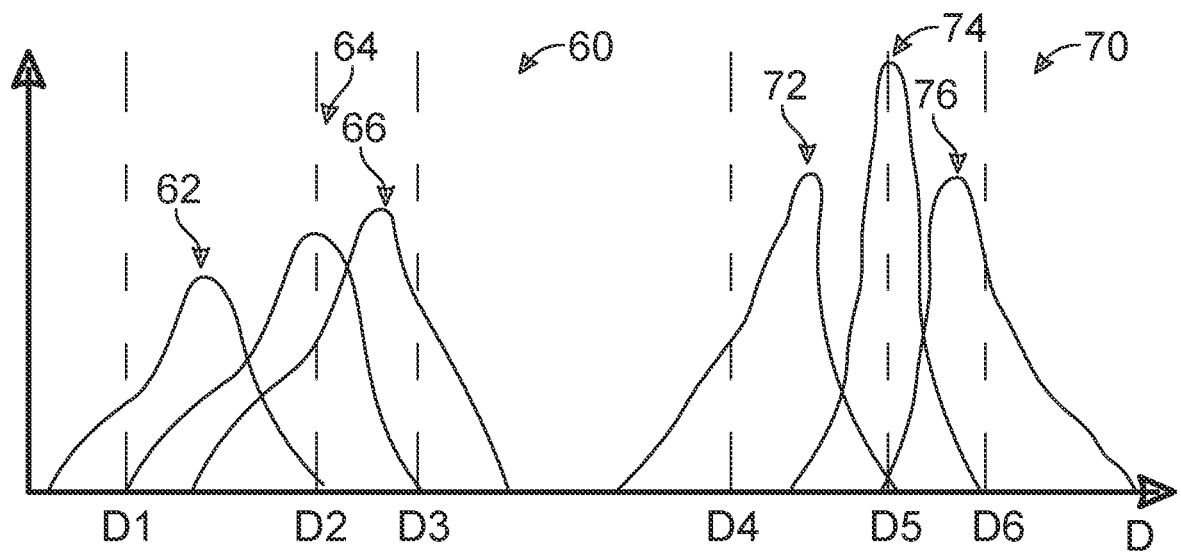
FIG. 4B is a schematic graph showing a Modulation Transfer Function plot for a phase-shift structure in a lens with dual focal regions.

In some additional embodiments, the ophthalmic lens 10 may be configured to utilize the phase-shift structure 30 for reducing chromatic aberration in a bifocal or multifocal application. For example, referring to FIG. 4B, in some embodiments, the ophthalmic lens 10 may provide a bifocal correction with two separate focal regions, as indicated by portion 60 and portion 70 in FIG. 4B. In portion 60, the peak of the first curve 62 and the peak of the third curve 66 are respectively moved towards the peak of the second curve 64. The bifocal correction can be either refractive or diffractive. Referring to portion 70 of FIG. 4B, the phase-shift structure 30 may be configured to shift the peak of the first curve 72 from distance D4 (along the optical axis 18) towards the second curve 74 at distance D5. The peak of the third curve 76 is shifted from distance D6 towards the second curve 74 at distance D5. Stated differently, the focal positions defined by the wavelengths in the range between a fourth wavelength (of the first curve 72) and a sixth wavelength (of the third curve 76) are at least partially converged towards a focal position defined by the wavelength of the second curve 74.

Figure 5:
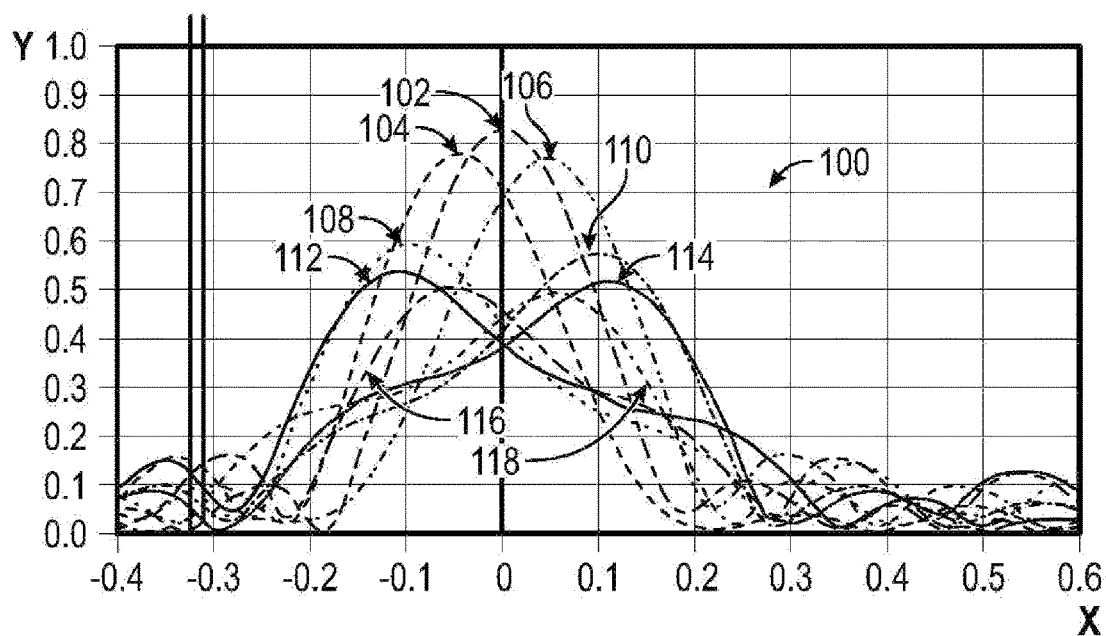
FIG. 5 is a schematic graph illustrating the amount of focus shift in an example ophthalmic lens, for incident radiation at different wavelengths.

Different amounts of phase shift result in different through-focus optical performance. Referring to graph 100 in FIG. 5, the through-focus relationship between different amounts of phase shifts is shown. The Y-axis in FIG. 5 depicts the modulation transfer function (MTF), reflecting the magnitude of transmission of the incident radiation I. The X-axis in FIG. 5 depicts the focus shift or distance from the retina. Trace 102 illustrates the MTF for zero step height. Referring to FIG. 5, traces 104, 106, 108, 110, 112, 114, 116, and 118 illustrate the respective MTF for step heights of +0.2, −0.2, +0.44, −0.44, +0.5, −0.5, +0.75, and −0.75 wavelengths, respectively. Trace 102 may be used as a reference point for a phase-shift region having a step height of zero wavelengths. As shown in FIG. 5, an increase in the absolute value of the step height results in a greater amount of focus shifting. Additionally, the respective traces for positive and negative phase shift veer in opposite directions. It is important to note that changing the step height of a phase-shift region will have differing effects on the chromatic properties for light at different wavelengths.

Figure 7:
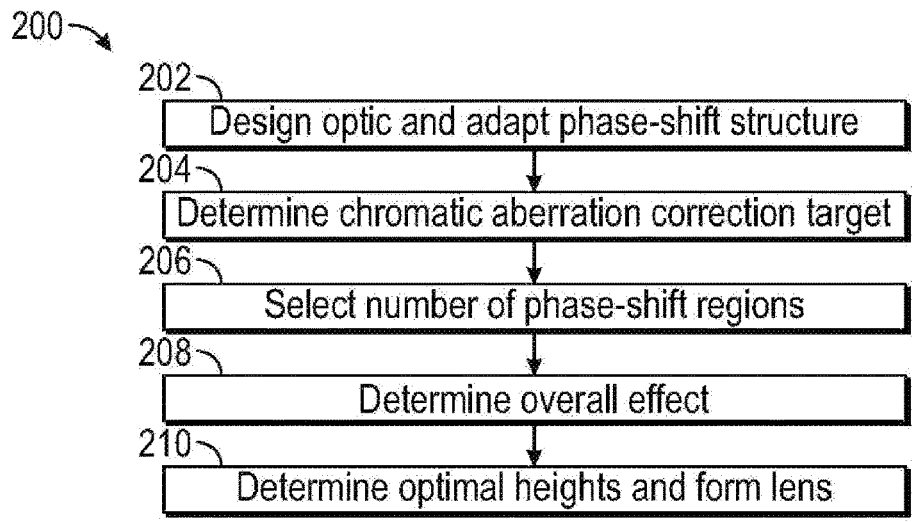
FIG. 7 is a schematic flowchart of a method for fabricating the ophthalmic lens for FIG. 1.

Referring to FIG. 7, a flow chart of method 200 for fabricating the ophthalmic lens 10 of FIG. 1 is shown. Diffractive extended depth-of-focus technologies rely on the add power for extension of focus, however, too much add power may make the clinical defocus performance discontinuous. The chromatic aberration compensation provided by diffractive technologies depends on the diffractive add power as well, making it difficult to tailor the chromatic property for each wavelength. The method 200 enables tailoring of lens polychromatic performance, chromatic correction/compensation profiles and the depth-of-focus extension.

Figure 6:
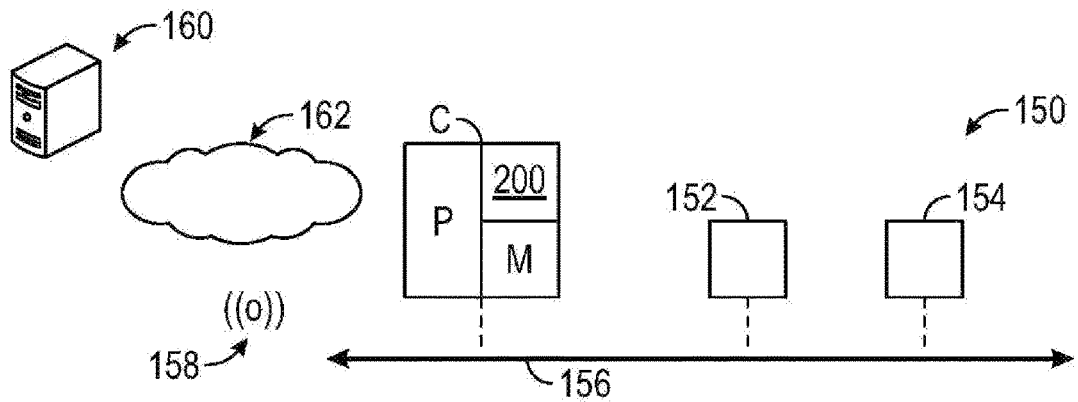
FIG. 6 is a schematic illustration of a system having a controller adapted to execute a method for fabricating the ophthalmic lens of FIG. 1.

Method 200 may be incorporated into and executed by a system 150, shown in FIG. 6. Referring to FIG. 6, the system 150 includes a controller C having at least one processor P and at least one memory M (or non-transitory, tangible computer readable storage medium) on which instructions may be recorded for executing at least a portion of the method 200. The memory M can store controller-executable instruction sets, and the processor P can execute the controller-executable instruction sets stored in the memory M. Execution of the instructions by the processor P causes the controller C to execute the method 200 described below.

Referring to FIG. 7, method 200 need not be applied in the specific order recited herein and some blocks may be omitted. Per block 202 of FIG. 7, the method 200 includes designing a phase-shift structure 30 (see FIGS. 1-2) having one or more phase-shift regions 32 for a first surface 14 of an optic 12, the first surface 14 being at least one of an anterior surface and a posterior surface. The phase-shift regions 32 may define respective initial step heights and are adapted to generate respective chromatic focal shifts.

Per block 204 of FIG. 7, the method 200 includes determining a chromatic aberration target for the optic 12. In one example, the chromatic aberration target is set to be within a range from −0.5 Diopter to +1.5 Diopters. Assuming that a typical human eye naturally has a chromatic aberration of +1.5 Diopters in the wavelength range of between about 450 nm and 650 nm, chromatic aberration correction may be 0.0 Diopter in the case of +1.5 Diopter chromatic aberration target and −2.0 Diopter in the case of a −0.5 Diopter chromatic aberration target. Note that the chromatic aberration target is the resultant value and the chromatic aberration correction is the compensation added to obtain the resultant value. Referring to FIG. 6, the system 150 may include a user interface 152 for collecting user data (e.g. chromatic aberration targets for a patient) from one or more clinical facilities or electronic medical record units. The system 150 may include a data management unit 154 for storing and/or facilitating transfer of the user data and other functions. The various components of the system 150 may be configured to communicate via a short-range network 156 and/or a long-range network 158. Referring to FIG. 6, the controller C may be in communication with a remote server 160 and/or a cloud unit 162, which may include one or more servers hosted on the Internet to store, manage, and process data. The cloud unit 162 may be a private or public source of information maintained by an organization, such as for example, a research institute, a company, a university and/or a hospital.

Referring to FIG. 6, the short-range network 156 may be a bus implemented in various ways, such as for example, a serial communication bus in the form of a local area network. The local area network may include, but is not limited to, a Controller Area Network (CAN), a Controller Area Network with Flexible Data Rate (CAN-FD), Ethernet, blue tooth, WIFI and other forms of data connection. The long-range network 158 may be a Wireless Local Area Network (LAN) which links multiple devices using a wireless distribution method, a Wireless Metropolitan Area Networks (MAN) which connects several wireless LANs or a Wireless Wide Area Network (WAN) which covers large areas such as neighboring towns and cities. Other types of connections may be employed.

Per block 206 of FIG. 7, the number or quantity of the phase-shift regions 32 meeting the chromatic aberration target is selected, based on the respective initial step heights of the phase-shift regions 32. Table I illustrates the initial step height in units of waves (unbounded or unwrapped) for incident radiation I characterized by wavelengths of: 0.40, 0.45, 0.50, 0.55, 0.60, 0.65 and 0.70 microns. The first row indicates the wavelength of radiation. Each subsequent row shows equivalent step height values in units of waves. The first column shows initial step height in microns.

TABLE I

| Physical Step Height (microns) | Wavelength (microns) | | | | | | |
|---|---|---|---|---|---|---|---|
| | 0.40 | 0.45 | 0.50 | 0.55 | 0.60 | 0.65 | 0.70 |
| −5.04 | −2.75 | −2.44 | −2.20 | −2.00 | −1.83 | −1.69 | −1.57 |
| −4.54 | −2.48 | −2.20 | −1.98 | −1.80 | −1.65 | −1.52 | −1.41 |
| −4.03 | −2.20 | −1.96 | −1.76 | −1.60 | −1.47 | −1.35 | −1.26 |
| −3.53 | −1.93 | −1.71 | −1.54 | −1.40 | −1.28 | −1.18 | −1.10 |
| −3.02 | −1.65 | −1.47 | −1.32 | −1.20 | −1.10 | −1.02 | −0.94 |
| −2.52 | −1.38 | −1.22 | −1.10 | −1.00 | −0.92 | −0.85 | −0.79 |
| −2.02 | −1.10 | −0.98 | −0.88 | −0.80 | −0.73 | −0.68 | −0.63 |
| −1.51 | −0.83 | −0.73 | −0.66 | −0.60 | −0.55 | −0.51 | −0.47 |
| −1.01 | −0.55 | −0.49 | −0.44 | −0.40 | −0.37 | −0.34 | −0.31 |
| −0.50 | −0.28 | −0.24 | −0.22 | −0.20 | −0.18 | −0.17 | −0.16 |
| 0.00 | 0.00 | 0.00 | 0.00 | 0.00 | 0.00 | 0.00 | 0.00 |
| 0.50 | 0.28 | 0.24 | 0.22 | 0.20 | 0.18 | 0.17 | 0.16 |
| 1.01 | 0.55 | 0.49 | 0.44 | 0.40 | 0.37 | 0.34 | 0.31 |
| 1.51 | 0.83 | 0.73 | 0.66 | 0.60 | 0.55 | 0.51 | 0.47 |
| 2.02 | 1.10 | 0.98 | 0.88 | 0.80 | 0.73 | 0.68 | 0.63 |
| 2.52 | 1.38 | 1.22 | 1.10 | 1.00 | 0.92 | 0.85 | 0.79 |
| 3.02 | 1.65 | 1.47 | 1.32 | 1.20 | 1.10 | 1.02 | 0.94 |
| 3.53 | 1.93 | 1.71 | 1.54 | 1.40 | 1.28 | 1.18 | 1.10 |
| 4.03 | 2.20 | 1.96 | 1.76 | 1.60 | 1.47 | 1.35 | 1.26 |
| 4.54 | 2.48 | 2.20 | 1.98 | 1.80 | 1.65 | 1.52 | 1.41 |
| 5.04 | 2.75 | 2.44 | 2.20 | 2.00 | 1.83 | 1.69 | 1.57 |
| 4.91 | 2.68 | 2.38 | 2.15 | 1.95 | 1.79 | 1.65 | 1.53 |

The system 10 is configured optimize the depth of focus extension and chromatic performance simultaneously, by selecting optimal physical step height(s) for one or multiple-step phase-shift designs. For a physical step height, its corresponding optical path difference (the key optical parameter) is different for different wavelengths when being expressed in unit of waves. And hence its depth of focus extension and chromatic property are different for different wavelengths. The physical step height may be calculated as: physical step height=step height in waves×wavelength/(refractive index of the IOL material−refractive index of aqueous humor). Referring to line 2 of Table I, for a physical step height of −5.04 microns, the equivalent step height in unit of waves is −2.00 waves for light having a wavelength of 0.55 micron. This is assuming the respective refractive index of the IOL material and aqueous humor is 1.5542 and 1.336, respectively. Thus, physical height is: [−2.00 waves×0.55 microns/(1.5542−1.336)]=−5.04 microns. Similarly, for a step size of −5.04 microns, the equivalent step height is −1.69 waves for light having a wavelength of 0.65 micron and −2.44 waves for light having a wavelength of 0.45 micron.

In order to optimize the process, the respective initial step heights of the phase-shift regions 32 may be bounded or wrapped within a minimum parameter and a maximum parameter. The wrapping process helps to save computing time and yields a better optimization. Complex optical systems are challenging to model. By tabulating the chromatic properties of phase-shift within minimum and maximum ranges, the wrapping process makes the modeling process and optimization considerably more efficient. Table II below illustrates bounded step height in unit of waves (originating from Table I) that are bounded between a maximum parameter and a minimum parameter. In this example, the minimum parameter is set as negative 0.5 wavelength units and the maximum parameter is set as positive 0.5 wavelength units. The bounding may be accomplished by the following mathematical function:

Bounded Step Height=Unbounded Step Height−[Unbounded Step Height Rounded to the Nearest Integer]

For example, comparing line 1 of Table I with line 1 of Table II, an unbounded step height of −2.75 waves results in a bounded step height of +0.25 waves, both at a wavelength of 0.4 microns.

TABLE II

| Physical Step Height (microns) | Wavelength (microns) | | | | | | |
|---|---|---|---|---|---|---|---|
| | 0.4 | 0.45 | 0.5 | 0.55 | 0.6 | 0.65 | 0.7 |
| −5.04 | 0.25 | −0.44 | −0.20 | 0.00 | 0.17 | 0.31 | 0.43 |
| −4.54 | −0.48 | −0.20 | 0.02 | 0.20 | 0.35 | 0.48 | −0.41 |
| −4.03 | −0.20 | 0.04 | 0.24 | 0.40 | −0.47 | −0.35 | −0.26 |
| −3.53 | 0.08 | 0.29 | 0.46 | −0.40 | −0.28 | −0.18 | −0.10 |
| −3.02 | 0.35 | −0.47 | −0.32 | −0.20 | −0.10 | −0.02 | 0.06 |
| −2.52 | −0.38 | −0.22 | −0.10 | 0.00 | 0.08 | 0.15 | 0.21 |
| −2.02 | −0.10 | 0.02 | 0.12 | 0.20 | 0.27 | 0.32 | 0.37 |
| −1.51 | 0.18 | 0.27 | 0.34 | 0.40 | 0.45 | 0.49 | −0.47 |
| −1.01 | 0.45 | −0.49 | −0.44 | −0.40 | −0.37 | −0.34 | −0.31 |
| −0.50 | −0.28 | −0.24 | −0.22 | −0.20 | −0.18 | −0.17 | −0.16 |
| 0.00 | 0.00 | 0.00 | 0.00 | 0.00 | 0.00 | 0.00 | 0.00 |
| 0.50 | 0.28 | 0.24 | 0.22 | 0.20 | 0.18 | 0.17 | 0.16 |
| 1.01 | −0.45 | 0.49 | 0.44 | 0.40 | 0.37 | 0.34 | 0.31 |
| 1.51 | −0.18 | −0.27 | −0.34 | −0.40 | −0.45 | −0.49 | 0.47 |
| 2.02 | 0.10 | −0.02 | −0.12 | −0.20 | −0.27 | −0.32 | −0.37 |
| 2.52 | 0.38 | 0.22 | 0.10 | 0.00 | −0.08 | −0.15 | −0.21 |
| 3.02 | −0.35 | 0.47 | 0.32 | 0.20 | 0.10 | 0.02 | −0.06 |
| 3.53 | −0.08 | −0.29 | −0.46 | 0.40 | 0.28 | 0.18 | 0.10 |
| 4.03 | 0.20 | −0.04 | −0.24 | −0.40 | 0.47 | 0.35 | 0.26 |
| 4.54 | 0.48 | 0.20 | −0.02 | −0.20 | −0.35 | −0.48 | 0.41 |
| 5.04 | −0.25 | 0.44 | 0.20 | 0.00 | −0.17 | −0.31 | −0.43 |
| 4.91 | −0.32 | 0.38 | 0.15 | −0.05 | −0.21 | −0.35 | −0.47 |

As discussed above, the system 10 and associated methods may be configured to simultaneously optimize both the depth of focus extension as well as the reduction in chromatic aberration for a given lens through the incorporation of one or more phase-shift regions having defined physical step heights. However, as also previously discussed, the effect of a physical step height of a phase-shift region on incoming light is a function of the particular wavelength of the light. Thus, selecting a particular step height may cause light falling within a first particular wavelength range to be shifted along the optical axis differently from light falling within a second particular wavelength range. Therefore, by manipulating both the number of phase-shift regions as well as the physical step heights of each of those phase-shift regions in a concerted fashion, the overall depth of focus for a given lens may be extended, while also at the same time reducing the amount of chromatic dispersion along the optical axis of light across the visual spectrum.

For example, the human eye has approximately −1.2 Diopter defocus for blue wavelength (0.45 microns) and approximately 0.3 Diopter defocus for red wavelength (0.65 microns). Thus, the total chromatic aberration is 1.5 diopter from 0.45 microns to 0.65 microns. Referring to Table III below (same as line 2 of Table II), if physical step height of −5.04 microns is selected, which corresponds to a zero waves step height for light at a wavelength of 0.55 microns, the corresponding step height is −0.44 waves at a wavelength of 0.45 microns and 0.31 waves at a wavelength of 0.65 microns. Accordingly, while the light at a wavelength of 0.55 microns may not be shifted along the optical axis, the light at wavelengths of 0.45 microns and 0.65 microns are expected to be shifted along the optical axis, and more specifically, converged towards the 0.55 micron wavelength light, and thereby reducing the total amount of chromatic aberration. In this specific example, a chromatic aberration correction of approximately 0.3 Diopter and 0.2 Diopter for light having a wavelength of 0.45 microns and 0.65 microns, respectively may be achieved, which may be determined by calculations performed by optical modeling software commercially available to one skilled in the art. Hence, this would reduce the longitudinal chromatic aberration of the human eye by approximately 0.5 Diopter. Additionally, to help illustrate this specific example, as can be seen in approximation from FIG. 5, trace 110 (representing the MTF for a step height of −0.44 waves at 0.45 microns wavelength) is shifted by about 0.1 mm along the optical axis, which corresponds to approximately 0.3 Diopters. Similarly, the step height of 0.31 waves at 0.65 microns wavelength, corresponding to a trace on FIG. 5 that would be somewhere between traces 104 and 108, is shifted by less than about 0.1 mm in the opposite direction along the optical axis, which corresponds to approximately 0.2 Diopters. The optical effects of this exemplary embodiment are generally illustrated in FIG. 3.

TABLE III

| Physical Step Height (microns) | Wavelength (microns) | | | | | | |
|---|---|---|---|---|---|---|---|
| | 0.4 | 0.45 | 0.5 | 0.55 | 0.6 | 0.65 | 0.7 |
| −5.04 | 0.25 | −0.44 | −0.20 | 0.00 | 0.17 | 0.31 | 0.43 |

As previously noted, graph 40 of FIG. 3 shows a first curve 42, a second curve 44 and a third curve 46, representing a first wavelength, a second wavelength and a third wavelength, respectively, in the absence of a phase-shift structure 30. For example, the first wavelength, the second wavelength and the third wavelength may be 450 nm, 550 nm and 650 nm, respectively (corresponding to Table III). The respective peaks of the first curve 42, the second curve 44 and the third curve 46 are separated along the optical axis 18 due to the effect of chromatic aberration. The phase-shift steps of the phase-shift structure 30 cause the first curve 42 to shift in direction 43 towards the second curve 44, and the third curve 46 to shift in direction 45 towards the second curve 44, effectively reducing the chromatic aberration of the eye by approximately 0.5 Diopter. Graph 50 of FIG. 3 shows the final effect of the phase-shift, with the respective peaks of the first curve 52 and the third curve 56 converging towards the second curve 54, reducing the longitudinal chromatic aberration and improving vision quality.

In one example, the chromatic aberration target may be set to 0.7 Diopter, according to block 204 of method 200, and the controller C may be configured to select two as the quantity or number of phase-shift regions 32 to be employed, according to block 206 of the method 200. Here, the following pairs of initial phase-shift regions may result in a cumulative correction amount of 0.7: (+1.0, −0.3), (+0.5, +0.2), (+0.3, +0.4). In each of these examples, the pairs add up to the total correction amount. Other combinations may be employed.

Per block 208 of FIG. 7, the method 200 further includes determining an overall interaction effect of the phase-shift regions 32, such as optical interaction of light affected by the one or more phase-shift regions 32 and the resulting effect on light of particular wavelengths (e.g., first wavelength of 450 nm, second wavelength of 550 nm, and third wavelength of 650 nm). To determine the overall interaction effect, the controller C may be configured to employ an optical model of the eye available to those skilled in the art. For example, the controller C may perform optical modeling analysis to determine how the optical design having the phase-shift regions 32 will meet the desired target chromatic aberration correction amount and overall depth of focus extension. Such optical modeling may be performed by optical design software, such as provided by ZEMAX, available to one skilled in the art. The optical model may be of varying anatomical accuracy, including single, three and four refracting surface variants. The optical model may incorporate features such as aspheric surfaces, tilts and decentrations, wavelength-dependent media and curved retinas. The optical model may be based on population averages and adaptable to account for age, gender, ethnicity and other factors. The optical model may be customized for a specific patient when ocular biometry and other specific data are available. Alternatively, to determine the overall interaction effect, the controller C may be configured to perform Finite Element Analysis (FEA) simulations using software available to those skilled in the art.

Per block 210 of FIG. 7, the method 200 further includes determining respective optimal heights of the phase-shift regions 32 based in part on the overall interaction effect, via the controller C. For example, based on the initial chromatic aberration correction and/or depth of focus extension performance determined by the optical modeling, iterative modifications to the number and/or step heights of the phase-shift regions 32 may be completed to optimize optical performance (e.g., chromatic aberration correction and/or depth of focus extension). Also, per block 210, the optic 12 is formed with the phase-shift regions 32 having the respective optimal heights. Referring to FIGS. 1 and 2, forming the optic 12 with the phase-shift structure 30 may include: forming the inner refractive region 20 defining a first nominal optical power and the outer refractive region 22 defining a second nominal optical power, the inner refractive region 20 extending from an inner boundary 24 and the outer refractive region 22 extending from an outer boundary 26. The phase-shift structure 30 may be positioned between the inner refractive region 20 and the outer refractive region 22, the phase-shift structure 30 extending from the inner boundary 24 to the outer boundary 26. The optic 12 may be formed with a suitable material available to those skilled in the art.

In one example, the optic 12 is formed from a cross-linked copolymer of 2-phenylethyl acrylate and 2-phenylethyl methacrylate.

Figure 8:
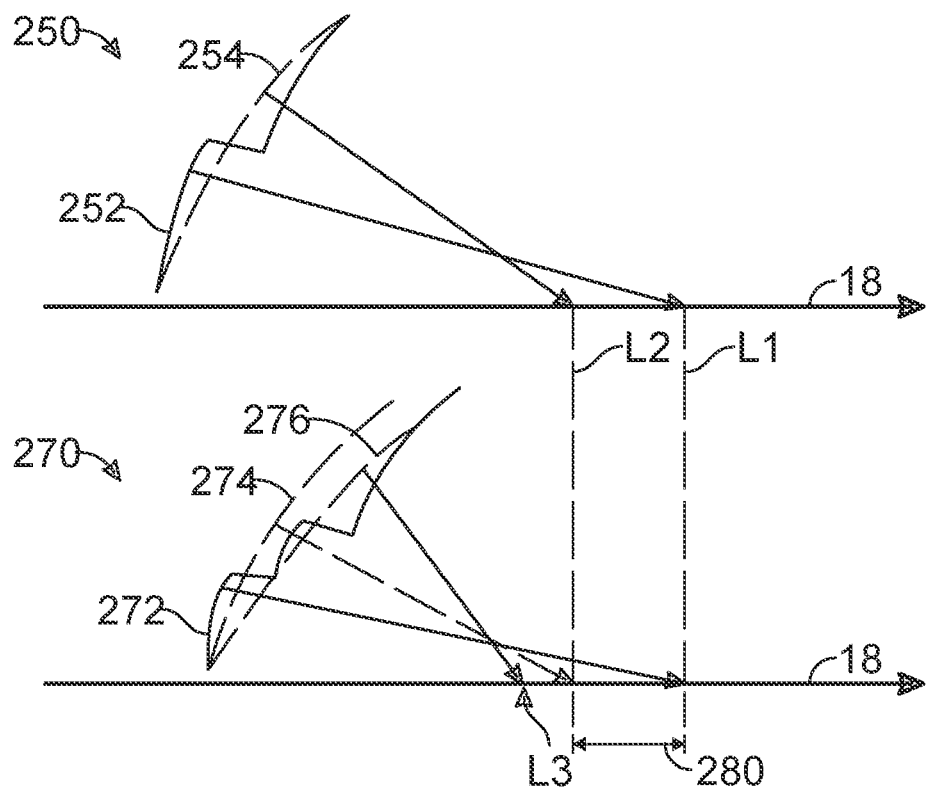
FIG. 8 is a schematic diagram illustrating extension of depth of focus for a wavefront incident on a surface of the ophthalmic lens of FIG. 1.

The ophthalmic lens 10 of FIG. 1 may be configured to enhance depth of focus extension along targeted directions by aligning the depth of focus produced by multiple ones of the phase-shift regions 32 in a direction of extension, while also simultaneously providing the targeted amount of chromatic aberration correction. In other words, the depth of focus extension works in conjunction with correction of chromatic aberration. Referring to FIG. 8, diagram 250 shows a first wavefront 252 focusing at the retina location L1. The direction of phase-shift, in terms of whether the phase-shift is advancing or delay of the wavefront, may be employed to control the depth of focus extension in front of or behind the retina location L1. After an initial phase-shift, a second wavefront 254 is generated that shifts the light energy to a second location L2. The second location L2 is in front of the retina location L1 and therefore increases the visual extension towards intermediate vision and near vision.

Referring to FIG. 8, diagram 270 shows the effect of multiple phase steps aligned in the direction of extension, for an ophthalmic lens 10 with two phase-shift regions 32. A first wavefront 272 focuses at the retina location L1. The initial phase-shift generates a second wavefront 274 that shifts the light energy to a second location L2, in front of the retina location L1. An additional phase-shift results in a third wavefront 276 that focuses at the third location L3, thereby extending the depth of focus in the region 280.

Figure 9:
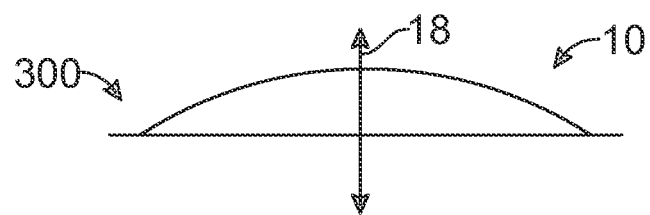
FIG. 9 is a schematic illustration of an example base profile that may be employed in the phase-shift structure of FIG. 1.

The profile of the ophthalmic lens 10 of FIGS. 1-2 may be characterized or defined by superposition of a base profile ($P_{base}$) and an auxiliary profile ($P_{aux}$), such that: $P_{sag}=[P_{base}+P_{aux}]$. Here, $P_{sag}$ denotes a sag of the surface of the ophthalmic lens 10 as a function of radial distance from the optical axis 18. FIG. 9 shows an example of a base profile 300 for the ophthalmic lens 10. The base profile 300 may be spherical or aspherical. The base profile 300 may be toric to mitigate corneal astigmatism. The shape of the base profile 300 may be selected based on the application at hand.

Figure 10:
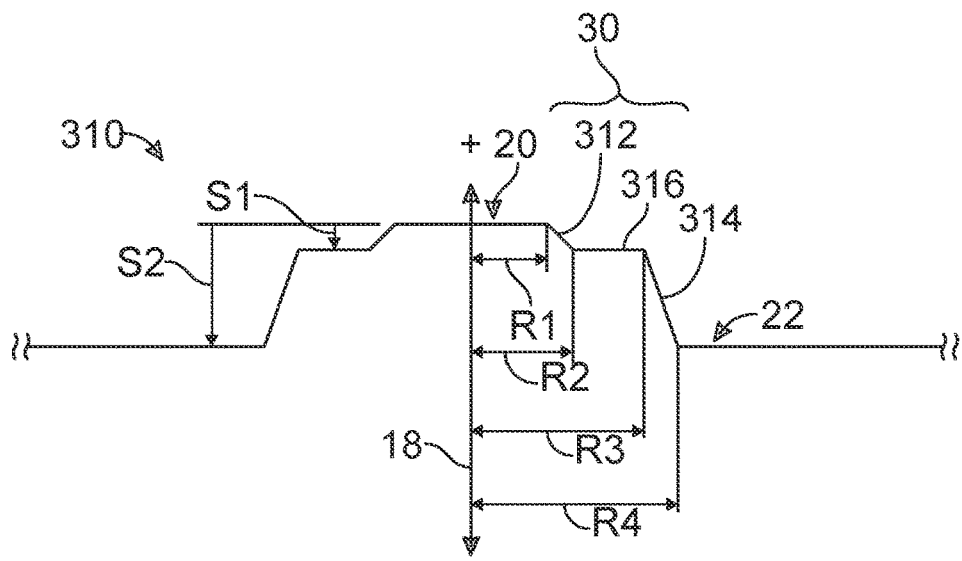
FIGS. 10-12 are schematic illustrations of various example auxiliary profiles that may be employed in the phase-shift structure of FIG. 1.
Figure 11:
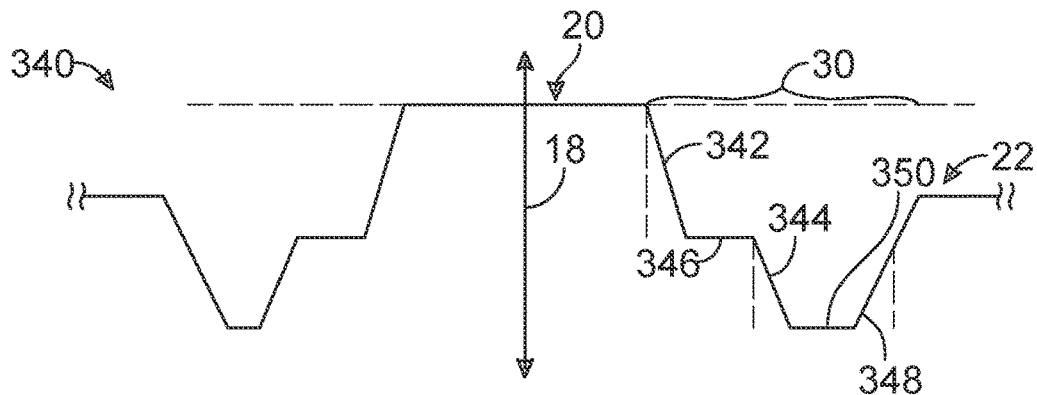
Figure 12:
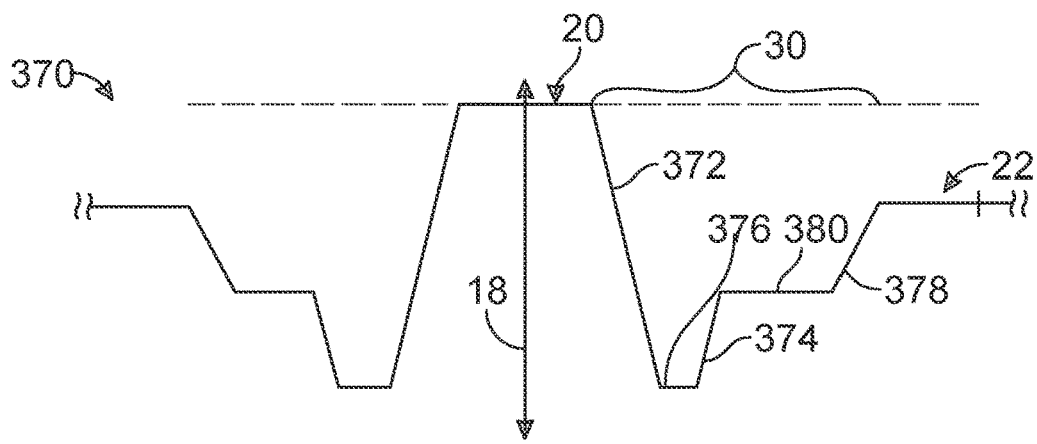

Referring now to FIGS. 10-12, various examples of auxiliary profiles are shown for the phase-shift structure 30, relative to the optical axis 18, between the inner refractive region 20 and the outer refractive region 22. Referring to FIG. 10, a first auxiliary profile 310 provides a phase-shift structure 30 that increases linearly from the inner refractive region 20 to the outer refractive region 22. The first auxiliary profile 310 includes a first phase-shift region 312 and a second phase-shift region 314, separated by a first plateau 316. The first phase-shift region 312 and the second phase-shift region 314 define a first step height 51 and a second step height S2, respectively. Referring to FIG. 10, the first phase-shift region 312 extends between a first radial distance R1 and a second radial distance R2 from the optical axis 18. the second phase-shift region 314 extends between a third radial distance R3 and a fourth radial distance R4 from the optical axis 18.

Referring to FIG. 11, the second auxiliary profile 340 includes a first phase-shift region 342 and a second phase-shift region 344, separated by a first plateau 346. The second auxiliary profile 340 includes a third phase-shift region 348 that may be spaced from the second phase-shift region 344 by a second plateau 350. Referring to FIG. 11, the first phase-shift region 342 and the second phase-shift region 344 extend in the same direction. The third phase-shift region 348 extends in an opposite direction. The inclusion of multiple steps with optimized heights increases the magnitude and flexibility of targeting a desired chromatic performance.

Referring to FIG. 12, a third auxiliary profile 370 includes a first phase-shift region 372 and a second phase-shift region 374 separated by a first plateau 376. The third auxiliary profile 370 includes a third phase-shift region 378 that may be spaced from the second phase-shift region 374 by a second plateau 380. Referring to FIG. 12, the second phase-shift region 374 and the third phase-shift region 378 extend in the same direction. The first phase-shift region 372 extends in an opposite direction. The directionality of the multiple steps enables flexibility in targeting a desired chromatic performance.

Figure 13:
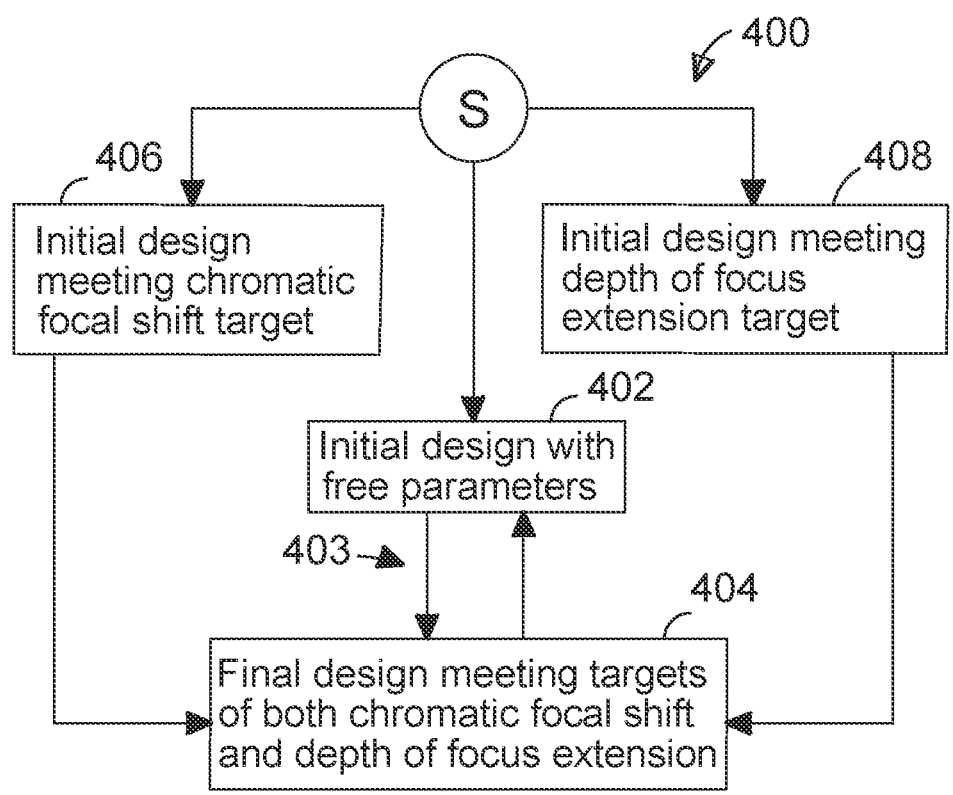
FIG. 13 is a schematic flowchart of a method executable by the controller of FIG. 1.

In some embodiments, the number of phase-shift steps and the optimal step heights are determined by meeting the targets of both chromatic focal shift and depth of focus extension. As illustrated by the flow chart of method 400 shown in FIG. 13, the realization of such embodiment may be started from an initial set of parameters targeting desirable chromatic focal shift, desirable depth of focus extension or free parameters. In one example, per block 402, an initial design with free parameters (number of steps and step heights) is selected. The number of steps and step heights may be adjusted iteratively (as indicated by lines 403) until a final design is reached that meets the targets of both chromatic focal shift and depth of focus extension, as shown in block 404. In another example, per block 406 of FIG. 13, an initial design is selected with parameters (number of steps and step heights) meeting the targeted chromatic focal shift. In order to meet the target of depth of focus extension, more steps may be added and all the step heights may be adjusted accordingly, until a final design is reached, per block 404, that meets the targets of both chromatic focal shift and depth of focus extension. In another example, per block 408, an initial design is selected with parameters (number of steps and step heights) meeting the targeted depth of focus extension. In order to meet the target of chromatic focal shift, more steps may be added and all the step heights may be adjusted until a final design is reached, per block 404, that meets the targets of both chromatic focal shift and depth of focus extension.

In summary, referring to FIG. 1, the phase-shift regions 32 are adapted to generate respective chromatic focal shifts such that an incident radiation I in a respective wavelength range at least partially converges towards a focal position of a respective selected wavelength. The inclusion of one or more phase-shift regions 32 with optimized heights changes the polychromatic property and depth of focus performance of the ophthalmic lens 10. The respective optimal heights of the phase-shift regions are based in part on the respective initial step heights of the phase-shift regions 32 and an overall interaction effect accounting for interaction between the respective initial step heights.

The controller C of FIG. 6 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A method for fabricating an ophthalmic lens, the method comprising:
   designing a phase-shift structure with one or more phase-shift regions for a first surface of an optic, the first surface being at least one of an anterior surface and a posterior surface;
   optimizing a depth-of-focus extension of the optic in a respective wavelength range by adapting the one or more phase-shift regions to generate respective chromatic focal shifts such that an incident radiation in the respective wavelength range at least partially converges towards a focal position of a respective selected wavelength,
   optimizing a depth-of-focus extension of the optic in additional respective wavelength ranges by adapting the one or more phase-shift regions to generate additional respective chromatic focal shifts such that the incident radiation in the additional respective wavelength ranges at least partially converge toward focal positions of additional respective selected wavelengths, the one or more phase-shift regions defining respective initial step heights after optimizing the depth-of-focus extensions;
   setting a chromatic aberration target for the optic to be within a range extending from −0.5 to 1.5 Diopters;
   selecting a quantity of the one or more phase-shift regions meeting the chromatic aberration target;
   determining an overall interaction effect of the respective initial step heights;
   modifying the respective initial step heights of the one or more phase-shift regions based in part on the overall interaction effect, wherein the modifying the respective initial step heights comprises iteratively modifying the respective initial step heights, via optical modeling, to meet the chromatic aberration target and the depth-of-focus extensions; and
   forming the optic with the one or more phase-shift regions having the respective optimal heights.

2. The method of claim 1, further comprising:
   bounding the respective initial step heights within a minimum parameter and a maximum parameter, prior to determining the overall interaction effect.

3. The method of claim 2, further comprising:
   setting the minimum parameter as negative 10 micron; and
   setting the maximum parameter as positive 10 micron.

4. The method of claim 1, further comprising: forming the optic from a cross-linked copolymer of 2-phenylethyl acrylate and 2-phenylethyl methacrylate.

5. The method of claim 1, wherein the respective selected wavelength includes a first selected wavelength, the method further comprising: setting the first selected wavelength to be around 550 nm.

6. The method of claim 1, wherein forming the optic with the phase-shift structure includes:
   forming an inner refractive region defining a first nominal optical power and an outer refractive region defining a second nominal optical power, the inner refractive region extending from an inner boundary and the outer refractive region extending from an outer boundary; and
   positioning the phase-shift structure between the inner refractive region and the outer refractive region, the phase-shift structure extending from the inner boundary to the outer boundary.

7. The method of claim 1,
   wherein adapting the one or more phase-shift regions to generate respective chromatic focal shifts and additional respective chromatic focal shifts comprises aligning the one or more phase-shift regions in a direction of extension, the phase-shift structure being adapted to increase the depth-of-focus of the optic in the direction of extension.

8. The method of claim 1, wherein:
   the depth-of-focus extension of the optic is selected to be within a range from about 0.75 Diopter to about 3.0 Diopter.

9. A method for fabricating an ophthalmic lens, the method comprising:
   designing a phase-shift structure with one or more phase-shift regions for a surface of an optic having an initial set of parameters;
   optimizing a depth of focus extension of the optic in a respective wavelength range by adapting one or more of the initial set of parameters to a second set of parameters to generate respective chromatic focal shifts such that an incident radiation in the respective wavelength range at least partially converges towards a focal position of a respective wavelength;

optimizing a depth of focus extension of the optic in additional respective wavelength ranges by adapting the one or more of the second set of parameters to a third set of parameters to generate additional respective chromatic focal shifts such that the incident radiation in the additional respective wavelength ranges at least partially converge toward focal positions of additional respective selected wavelengths;

setting a chromatic aberration target for the optic to be within a range extending from −0.5 to 1.5 Diopters;

determining an overall interaction effect of the third set of parameters;

modifying one or more of the third set of parameters of the one or more phase-shift regions based in part on the overall interaction effect, wherein the modifying the one or more of the third set of parameters comprises iteratively modifying one or more of the third set of parameters, via optical modeling, to meet the chromatic aberration target and depth-of-focus extensions; and forming the optic with the one or more phase-shift regions having respective optimal parameters.

10. The method of claim 9, wherein the initial set of parameters comprise at least one of a quantity of one or more phase-shift regions or a step height of one or more phase-shift regions.

11. The method of claim 10, further comprising:
bounding the step heights of the initial set of parameters within a minimum parameter and a maximum parameter.

12. The method of claim 11, further comprising:
setting the minimum parameter as negative 10 micron; and
setting the maximum parameter as positive 10 micron.

13. The method of claim 9, further comprising: forming the optic from a cross-linked copolymer of 2-phenylethyl acrylate and 2-phenylethyl methacrylate.

14. The method of claim 9, wherein the respective selected wavelength includes a first selected wavelength, the method further comprising: setting the first selected wavelength to be around 550 nm.

15. The method of claim 9, wherein forming the optic with the phase-shift structure includes:
forming an inner refractive region defining a first nominal optical power and an outer refractive region defining a second nominal optical power, the inner refractive region extending from an inner boundary and the outer refractive region extending from an outer boundary; and positioning the phase-shift structure between the inner refractive region and the outer refractive region, the phase-shift structure extending from the inner boundary to the outer boundary.

16. The method of claim 9, wherein adapting the one or more initial set of parameters to a second set of parameters to generate respective chromatic focal shifts and the one or more second set of parameters to a third set of parameters to generate additional respective chromatic focal shifts comprises aligning the one or more phase-shift regions in a direction of extension, the phase-shift structure being adapted to increase the depth-of-focus of the optic in the direction of extension.

17. The method of claim 9, wherein:
the depth-of-focus extension of the optic is selected to be within a range from about 0.75 Diopter to about 3.0 Diopter.

* * * * *